(12) United States Patent
Van Kessel (10) Patent No.: US 10,147,312 B2
(45) Date of Patent: Dec. 4, 2018

(54) ACOUSTIC COMPUTING SYSTEMS FOR IMPLANT AND DERMAL DATA COMMUNICATION, POWER SUPPLY AND ENERGY STORAGE

(71) Applicant: INTERNATIONAL BUSINESS MACHINES CORPORATION, Armonk, NY (US)

(72) Inventor: Theodore G. Van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 288 days.

(21) Appl. No.: 14/745,601

(22) Filed: Jun. 22, 2015

(65) Prior Publication Data
US 2016/0133124 A1 May 12, 2016

Related U.S. Application Data

(63) Continuation-in-part of application No. 14/534,975, filed on Nov. 6, 2014.

(51) Int. Cl.
*A61B 5/00* (2006.01)
*G08C 23/02* (2006.01)
(Continued)

(52) U.S. Cl.
CPC ............ *G08C 23/02* (2013.01); *A61B 5/0031* (2013.01); *A61N 1/3787* (2013.01); *A61N 1/37217* (2013.01); *A61B 2560/0214* (2013.01)

(58) Field of Classification Search
None
See application file for complete search history.

(56) References Cited

U.S. PATENT DOCUMENTS

| | | | |
|---|---|---|---|
| 8,082,041 B1 * | 12/2011 | Radziemski | A61N 1/3787 607/33 |
| 2004/0172083 A1 * | 9/2004 | Penner | A61B 5/0031 607/35 |
| 2013/0328416 A1 * | 12/2013 | Whitworth | H02J 50/05 307/149 |

OTHER PUBLICATIONS

List of IBM Patents or Patent Applications Treated as Related—Date Filed: Jul. 27, 2015; 2 page.

(Continued)

*Primary Examiner* — Joel F Brutus
(74) *Attorney, Agent, or Firm* — Cantor Colburn LLP; Vazken Alexanian (57) ABSTRACT

Embodiments are directed to a method of implementing an acoustic computing system for implant or dermal data communication, power supply and energy storage. The method includes receiving, by a first acoustic computing element in a live medium, input acoustic vibration. The method further includes converting, by the first acoustic computing element, a first portion of the input acoustic vibration to energy that powers operation of the first acoustic computing element. The method further includes converting, by the first acoustic computing element, a second portion of the input acoustic vibration to stored energy of the first acoustic computing element. The method further includes converting, by the first acoustic computing element, a third portion of the input acoustic vibration to a first input data that is processed by the first acoustic computing element. The method further includes generating, by the first acoustic computing element, a first output acoustic vibration based on the first input data.

19 Claims, 6 Drawing Sheets

(51) Int. Cl.
*A61N 1/378* (2006.01)
*A61N 1/372* (2006.01)

(56) References Cited

OTHER PUBLICATIONS

Theodore G. Van Kessel, "Acoustic Computing Systems for Implant and Dermal Data Communication, Power Supply and Energy Storage," U.S. Appl. No. 14/534,975, Date Filed: Nov. 6, 2014.

* cited by examiner

ACOUSTIC COMPUTING SYSTEMS FOR IMPLANT AND DERMAL DATA COMMUNICATION, POWER SUPPLY AND ENERGY STORAGE

DOMESTIC PRIORITY

The present application is a continuation U.S. Nonprovisional application Ser. No. 14/534,975 filed on Nov. 6, 2014 titled "ACOUSTIC COMPUTING SYSTEMS FOR IMPLANT AND DERMAL DATA COMMUNICATION, POWER SUPPLY AND ENERGY STORAGE" Partner Marketing Based on an Expected Customer Visit", assigned to the assignee hereof and expressly incorporated by reference herein.

BACKGROUND

The present disclosure relates generally to implantable electronic medical devices. More specifically, the present disclosure relates to an acoustic computing system and network having at least one implant/dermal acoustic computing element, wherein the system/network enables implant and dermal data communication, power supply and energy storage.

Implantable electronic medical devices (i.e., "implants") have enabled significant advances in the treatment of many challenging medical conditions. One example is implantable pacemakers that stimulate the heart muscle to regulate its contractions. Another example is a cochlear implant, which is an electronic device that partially restores hearing in people who have severe hearing loss due to damage of the inner ear. A processor behind the ear captures and processes sound signals, which are transmitted to a receiver that is surgically placed under the skin. Some implants are bioactive, such as subcutaneous drug delivery devices in the form of implantable pills or drug-eluting stents. The increasing demand for implantable medical device technologies is fuelled by the growing elderly population and the general increase in chronic diseases.

Radio frequency (RF) tags have been demonstrated as implants that are capable of transmitting RF data from inside a patient to an external device capable of reading the transmitted signal. RF implant devices are typically used subcutaneously because their RF signals do not transmit well through an aqueous media over long distances (e.g., more than an inch or two) due to the rate at which an aqueous media attenuates and absorbs RF signals. Additionally, due to a variety of constraints (e.g., cost) the typical RF implant device is passive. Active RF implant devices require power to be supplied usually by internal batteries or inductive coupling to a power supply that is external to the patient. For inductive coupling implementations, the coupling efficiency is proportional to the size of the implanted device. RF implant devices also raise privacy concerns because of the possibility that they can they can be read without patient knowledge and consent.

SUMMARY

Embodiments are directed to a computing system configured to operate at least partially through a medium. The computing system includes a first acoustic computing element in the medium. The first acoustic computing element is configured to receive input acoustic vibration. The first acoustic computing element is further configured to convert a first portion of the input acoustic vibration to energy that powers operation of the first acoustic computing element. The first acoustic computing element is further configured to convert a second portion of the input acoustic vibration to stored energy of the first acoustic computing element. The first acoustic computing element is further configured to convert a third portion of the input acoustic vibration to a first input data that is processed by the first acoustic computing element. The first acoustic computing element is further configured to generate and transmit a first output acoustic vibration based on the first input data.

Embodiments are further directed to a method of implementing an acoustic computing system for implant or dermal data communication, power supply and energy storage. The method includes receiving, by a first acoustic computing element in a live medium, input acoustic vibration. The method further includes converting, by the first acoustic computing element, a first portion of the input acoustic vibration to energy that powers operation of the first acoustic computing element. The method further includes converting, by the first acoustic computing element, a second portion of the input acoustic vibration to stored energy of the first acoustic computing element. The method further includes converting, by the first acoustic computing element, a third portion of the input acoustic vibration to a first input data that is processed by the first acoustic computing element. The method further includes generating, by the first acoustic computing element, a first output acoustic vibration based on the first input data.

Additional features and advantages are realized through the techniques described herein. Other embodiments and aspects are described in detail herein. For a better understanding, refer to the description and to the drawings.

BRIEF DESCRIPTION OF THE SEVERAL VIEWS OF THE DRAWINGS

The subject matter which is regarded as the present disclosure is particularly pointed out and distinctly claimed in the claims at the conclusion of the specification. The foregoing and other features and advantages are apparent from the following detailed description taken in conjunction with the accompanying drawings in which:

In the accompanying figures and following detailed description of the disclosed embodiments, the various elements illustrated in the figures are provided with three or four digit reference numbers. The leftmost digit(s) of each reference number corresponds to the figure in which its element is first illustrated.

DETAILED DESCRIPTION

Various embodiments of the present disclosure will now be described with reference to the related drawings. Alternate embodiments may be devised without departing from the scope of this disclosure. It is noted that various connections are set forth between elements in the following description and in the drawings. These connections, unless specified otherwise, may be direct or indirect, and the present disclosure is not intended to be limiting in this respect. Accordingly, a coupling of entities may refer to either a direct or an indirect connection.

As previously noted herein, RF tags have been demonstrated as implants that are capable of transmitting RF data from inside a patient to an external device capable of reading the transmitted signal. RF implant devices are typically used subcutaneously because their RF signals do not transmit well through an aqueous media over long distances (e.g., more than an inch or two) due to the rate at which an aqueous media attenuates and absorbs RF signals. Additionally, due to a variety of constraints (e.g., cost) the typical RF implant device is passive. Active RF implant devices require power to be supplied usually by internal batteries or inductive coupling to a power supply that is external to the patient. For inductive coupling implementations, the coupling efficiency is proportional to the size of the implanted device. RF implant devices also raise privacy concerns because of the possibility that they can they can be read without patient knowledge and consent.

Turning now to a more general overview of the present disclosure, one or more disclosed embodiments provide an implant and/or dermal computing system and network that use high amplitude modulated or otherwise encoded acoustic vibration to safely and efficiently transmit power, data, instructions, etc. bi-directionally through the relevant medium. The disclosed implant/dermal acoustic computing system/network includes one or more implant or dermal elements, along with an external control system formed from external control electronics and an external transducer. The implant/dermal element according to the present disclosure is implemented as a miniaturized acoustic computing element having processor, energy storage, sensing and actuating capabilities. The implant/dermal acoustic computing element efficiently partitions received high amplitude modulated input acoustic vibration among the immediate power needs of the computing element, data/instructions and energy storage. The combination of efficient high amplitude acoustic input vibration and relatively small and efficient implant/dermal acoustic computing elements allows the implant/dermal element to partition a significant portion of the input acoustic vibration to energy storage, thereby enabling persistent operation over relatively long periods without needing a recharge. The persistent operation may last a few hours or a few years depending on a variety of factors, such as the tasks performed by the implant/dermal element, the particular design of the implant/dermal element, and others. In network configurations of the present disclosure, acoustic computing elements are configured to also exchange low amplitude acoustic power, data, instructions, etc. between each other. Thus, the present disclosure provides a comprehensive acoustic computing system and network for implant and dermal data communication, power supply and energy storage. The efficiency, intelligence, safety and flexibility of the disclosed system and network enable it to implement a wide variety of medical support functions for patients, including storing general medical records, storing specific medical condition data (e.g., that the patient is diabetic), performing drug delivery, stimulating muscles, providing identification data (e.g., a serial number) for other implanted elements such as an artificial hip, and others.

Turning now to a more detailed overview of the present disclosure, one or more embodiments provide an implant/dermal acoustic computing element that is capable of both being energized by an externally applied acoustic source and of communicating and responding acoustically to the source. The implant/dermal acoustic computing element is a physically small device (e.g., approximately one centimeters or less) that is encapsulated in a biocompatible material and may be placed in or on a medium, which may be a living organism such as a human or an animal. The implant/dermal acoustic computing element includes input and output piezoelectric elements that convert acoustic/mechanical vibration to electric signals and vice versa. Preferably, the acoustic vibration is in the ultrasonic wavelength region (e.g., 50 KHz) such that the physical size of the implant/dermal acoustic computing element is comparable to the length of the wavelength used, thereby improving coupling efficiency of the acoustic vibration. A preferred range for the ultrasonic region includes, but is not limited to, approximately 50 KHz to approximately 10 MHz.

In one or more embodiments of the present disclosure there is provided an acoustic computing system and/or network for dermal and implant data communication, power supply and energy storage. In its simplest configuration, the acoustic computing system includes at least one implantable miniaturized acoustic computing element having a transmitter/receiver that excites a piezoelectric material to emit or detect acoustic vibration, which is typically ultrasonic acoustic vibration that has been modulated or otherwise encoded with data and instructions. More specifically, the miniaturized acoustic computing element is configured to received modulated acoustic vibration, convert a portion of the received modulated acoustic vibration to received data/instruction, process the received data/instruction, convert a portion of received modulated acoustic vibration to power that is used to operate the acoustic computing element, convert a portion of the received modulated acoustic vibration to stored energy, convert processed data/instruction to output acoustic vibration (which may also be modulated or otherwise encoded) and transmit the output acoustic vibration. The acoustic computing element may be implanted in virtually any medium. In a typical application, the medium is a live organism, such as a human or an animal. Where the live organism is a human or an animal, the acoustic computing element may be placed in flesh (i.e., implanted), or on, within or just under the dermas.

The acoustic computing element may be provided with controllable sensor and actuator elements. The acoustic computing element controls the sensor to measure and/or detect a parameter of the medium, including, for example, a concentration of a target substance (e.g., a concentration of glucose in blood), a temperature, a pressure, a force, a magnetic field, an electric field, a biomarker and a chemical potential. As used in the present disclosure, the term biomarker refers generally to a measurable indicator of some biological state or condition, including providing an indication of the existence of a living organism. The acoustic computing element controls the actuator to cause an electrical or mechanical interaction with the medium. Examples of actuators include valves, nanoliter dispensers, and others. Examples of electrical interactions with the medium include a therapeutic electrical stimulation applied to the medium. Examples of mechanical interactions with the medium include controlling a nanoliter dispenser that dispenses fluids or releases a chemical to the medium.

An aspect of the present disclosure is the use of acoustic vibration to transmit signals through the medium. As previously noted herein, RF transmissions are capable of carrying data from inside a patient to an external device capable of reading the transmitted signal. However, RF-based implant devices are typically restricted to subcutaneous use because RF does not transmit efficiently over long distances (e.g., more than a few inches) due to absorption of the radio emissions in aqueous media. Acoustic vibration transmissions provide at least three features, namely, low power attenuation, low data attenuation and high safety. For example, it has been observed that the attenuation of ultrasonic vibration that travels approximately 6 inches through an aqueous medium is only approximately 20 percent. The safety of ultrasonic transmissions is demonstrated by the widespread use of ultrasonic imaging by medical professionals to view an unborn fetus in the womb. The high safety and low attenuation of acoustic vibration also enable a fourth feature of the present disclosure, which is the ability to safely and efficiently deliver relatively high power acoustic vibration to the implanted acoustic computing element.

The efficient (i.e., low attenuation) delivery of high power input acoustic vibration to the acoustic computing element enables the high power input acoustic vibration to be efficiently partitioned by the acoustic computing element among data processing, power supply and power storage. More specifically, the efficient high power, modulated input acoustic vibration efficiently wakes the implanted acoustic computing element up, delivers information, and has enough left over to provide power for current operation and storage. The actual amount of high power input acoustic vibration energy that is left for storage depends on the design and power consumption of the acoustic computing element, which, due to its miniaturized size, can be very low. Accordingly, it is anticipated that a single charge-up will allow an implant/dermal acoustic computing element to run for a very long time (e.g., for a year). After being powered up, the implant/dermal acoustic computing element is now free to perform sensing or actuating operations, or simply return data and/or instructions.

In addition to the implanted and/or dermal acoustic computing element, the acoustic computing system of the present disclosure includes a control system formed from a transducer and control electronics, both of which are external to the medium. The control electronics and external transducer generate the high power data/instruction modulated input acoustic vibration and transmits it into and through the medium to the implanted/dermal acoustic computing element. The control electronics and external transducer in turn receive data/instruction modulated output acoustic vibration transmitted by the implanted/dermal acoustic computing element. The outputs transmitted by implant/dermal acoustic computing element may be in response to an inquiry from the control electronics, or these outputs may be transmitted according to a predetermined transmission schedule regardless of whether control electronics are present. Control electronics is further coupled through other networks and systems such as the internet or cellular networks.

A benefit of the disclosed acoustic computing system is that it is inherently private because it cannot be read or perturbed without the knowledge, consent and cooperation of the patient. In general, the patient has to cooperate while someone actually places the external transducer against the patient's skin in order to read or otherwise interact with the implant/dermal acoustic computing element. This privacy feature enables the disclosed systems to be used to store confidential and sensitive information such as patient records. Such medical records can be easily updated, for example during a visit to the patient's doctor. They can also be conveniently accessed by an emergency response team if the patient is in an accident. Medical records stored by the disclosed system can be considerably more extensive and comprehensive than the general data a patient can provide verbally after an accident. Unlike medical emergency tags, the disclosed implanted/dermal acoustic computing elements cannot be lost.

The implant/dermal acoustic computing system may be implemented as a network wherein additional implant/dermal acoustic computing elements are provided. In the network configuration, implant/dermal acoustic elements may also transmit a modulated acoustic vibration between each other, thereby enabling the implant/dermal acoustic computing network to implement of a wide variety of coordinated activities. For example, a first implant/dermal acoustic computing element may, according to a predetermined schedule, sense blood sugar levels of a patient, and, upon sensing that blood sugar has risen above a predetermined level, send an instruction to a second implant/dermal acoustic computing element to dispense through a nanoliter dispenser (i.e., an actuator) a dose of medicine to the patient. Upon detecting that the volume of medicine in its nanoliter dispenser has fallen below a predetermined level, the second implant/dermal acoustic computing element may send via a modulated acoustic vibration transmission an instruction to the control electronics to send an email to the patient reminding them that they will be need to have the nanoliter dispenser refilled or replaced in the next 20 days. Additionally, the second implant/dermal acoustic computing element, upon detecting that its power is below a predetermined level, may send a power request to the first implant/dermal acoustic computing element. If the first implant/dermal acoustic computing element determines that it has stored power that it can spare, the first implant/dermal acoustic computing element may transmit power to the second implant/dermal acoustic computing element through an acoustic transmission.

Figure 1:
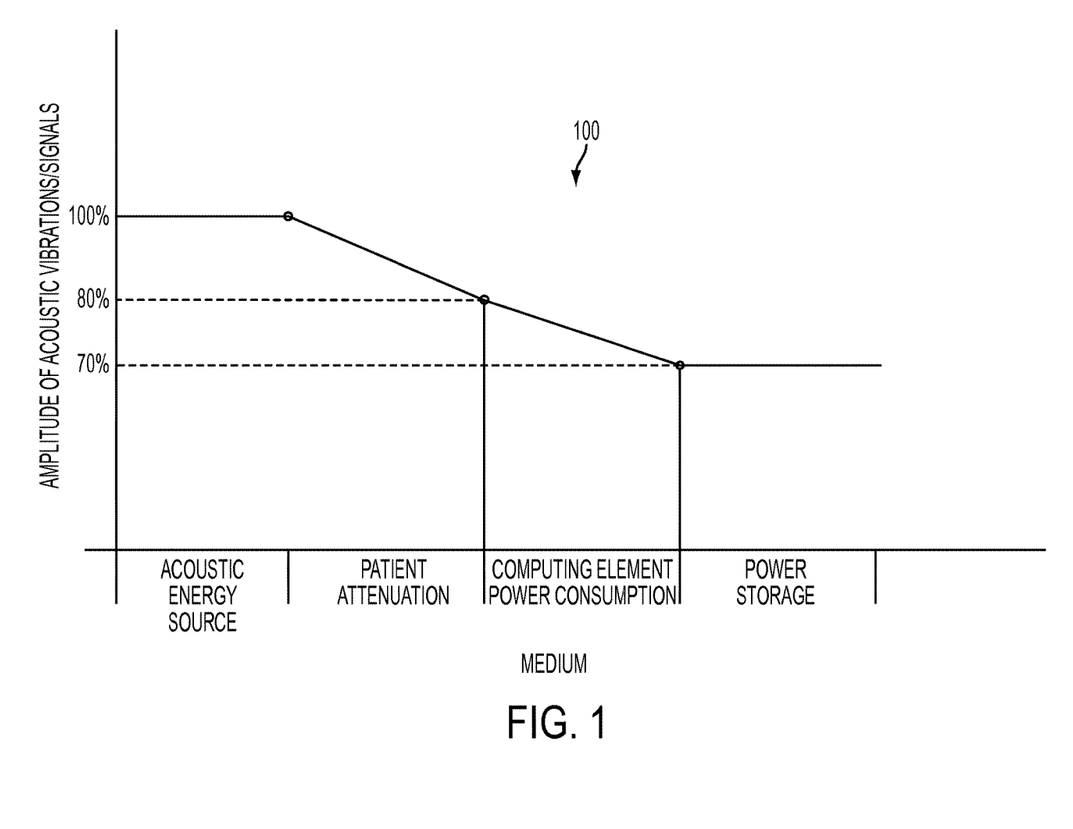
FIG. 1 is a diagram illustrating an allocation of input acoustic vibration/signals in accordance with one or more embodiments.

Turning now to a more detailed description of the present disclosure, FIG. 1 is a graphical diagram 100 that illustrates how high power input acoustic vibration may be allocated in accordance with one or more embodiments. In general, diagram 100 is a graph that shows the amplitude of modulated input acoustic vibration along a vertical axis, and the acoustic energy source and the various ways that modulated input acoustic vibration may be used by the implant/dermal acoustic computing element along a horizontal axis. For ease of illustration, the amplitudes of the modulated input acoustic vibration are shown as percentages, and it is assumed that the amplitude of the modulated acoustic vibration from an acoustic energy source is at 100 percent. As shown, the amplitude of the modulated input acoustic vibration leaves the acoustic energy source at 100 percent and travels through the medium, which in this example is a human patient. The human patient attenuates and reduces the amplitude of the modulated input acoustic vibration as it travels through the patient by 20 percent, down to 80 percent. The immediate operation of the implant/dermal computing element uses another 10 percent of the amplitude of the modulated input acoustic vibration such that 70 percent of the amplitude of the modulated input acoustic vibration is available to be stored for future operation.

FIG. 1 also illustrates graphically how the efficient (i.e., low attenuation) delivery of high power input acoustic vibration to the acoustic computing element enables the high power input acoustic vibration to be efficiently partitioned by the acoustic computing element among data processing, power supply and power storage. As previously noted, the amount of high power input acoustic vibration energy that is left for storage depends on the design and power consumption of the acoustic computing element, which, due to its miniaturized size, can be very low. Accordingly, it is anticipated that a single charge-up will allow an implant/dermal acoustic computing element to run for a very long time (e.g., for a year).

Figure 2:
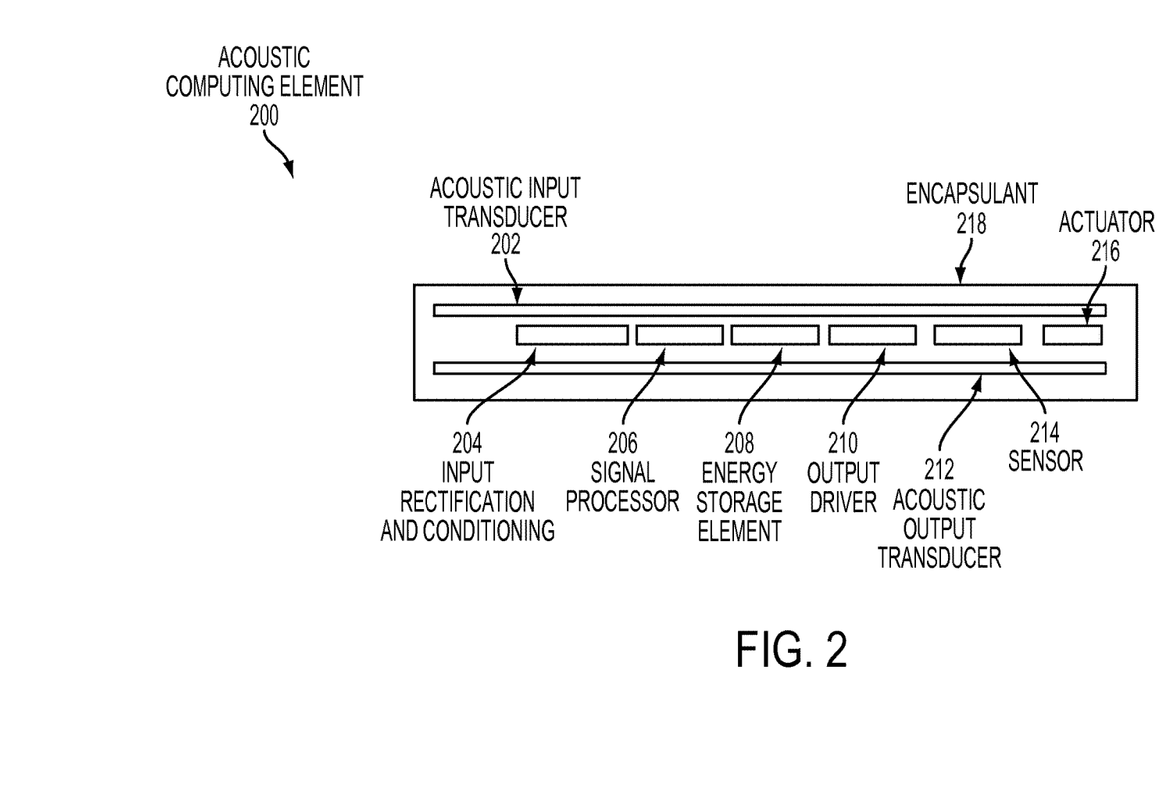
FIG. 2 is a schematic diagram of an implantable acoustic computing element in accordance with one or more embodiments.

FIG. 2 is a schematic diagram of an implantable acoustic computing element 200 in accordance with one or more embodiments. Implantable acoustic computing element 200 includes an acoustic input transducer 202, an input rectification and conditioning circuit 204, a signal processor 206, an energy storage element 208, an output driver 210, an acoustic output transducer 212, a sensor 214, an actuator 216 and an encapsulant 218, configured and arranged as shown. Acoustic computing element 200 includes at least one acoustic-to-electric conversion element or acoustic input transducer 202. Preferably, acoustic input transducer 202 is a piezoelectric material, but may also be a mechanical electric element such as an electret (i.e., a capacitive acoustic transducer) or magneto acoustic transducer. In one or more embodiments, the functionality of acoustic input transducer 202 and acoustic output transducer 210 may be integrated into a single input/output transducer element (not shown).

In operation, high power input acoustic vibration, which is preferably in the ultrasonic range from 5 KHz to 5 MHz, is converted to an alternating electric signal by input acoustic transducer 202. Input rectification and conditioning circuit 204, which is operationally connected to acoustic input transducer 202, receives the converted alternating electric signal and generates usable electric power. Input rectification and conditioning circuit 204 rectifies the alternating signal from acoustic input transducer 202 and produces a direct current source at a desired voltage. Input power rectification and conditioning circuit 204 in one or more embodiments further includes and is operationally connected to energy storage element 208, which may be implemented as a capacitor and a battery.

Acoustic input transducer 202 is operationally connected to signal processor 206 either directly or through input rectification and conditioning circuit 204. Signal processor 206 receives power through a connection to input rectification and conditioning circuit 204. Signal processor 206 conditions and extracts signal information that has been modulated on or otherwise encoded in the high amplitude input acoustic vibration. Signal processor 206 further provides a programmed response or output, which may also be modulated, to output driver 210. The conditioning performed by signal processor 206 includes signal buffering, amplification and windowing. Output driver 210 is operationally connected to input rectification and conditioning circuit 204 to provide a power source.

Signal processor 206 may be implemented as a simple hard wired programmed circuit or as a microprocessor. In one or more embodiments, signal processor 206 responds to acoustic input vibration according a predetermined set of instructions. In one or more embodiments, signal processor 206 is programmable and receives program instructions from the input acoustic vibration. The programmed set of instructions in signal processor 206 may include input decryption, output encryption, finite impulse filtration, Fourier transform signal processing, data retrieval, data processing, and sensor read/write operations.

Sensor 214 measures parameters that include, but are not limited to temperature, pressure, force, magnetic field, electric field and chemical potential. Sensor 214 is operationally connected to signal processor 206 and may be energized by energy storage element 208 or input rectification and conditioning circuit 204. Similarly, actuator 216 causes an electrical or mechanical action. Actuator 216 could be implemented, for example, as a valve or a nanoliter dispenser. Actuator 216 could also deliver a therapeutic electrical or mechanical stimulation. Actuator 216 is operationally connected to signal processor 206 and may be energized by energy storage element 208 or input rectification and conditioning circuit 204.

Acoustic output signals from signal processor 206 are emitted by acoustic output transducer 212. Output driver 210 provides amplification, impedance matching and isolation between signal processor 206 and acoustic output transducer 212. Acoustic output transducer 212 may be implemented as a piezoelectric material, but may also be implemented as a mechanical electric element such as an electret (i.e., a capacitive acoustic transducer) or magneto acoustic transducer. As previously noted, in one or more embodiments, the functionality of acoustic input transducer 202 and acoustic output transducer 210 may be integrated into a single input/output transducer element. Suitable piezoelectric materials for use as acoustic input transducers 202 and acoustic output transducer 212 include lead zirconate titanate (PZT), quartz, polyvinylidene fluoride (PVDF also known as Kynar), sodium potassium niobate ((K,Na)NbO$_3$), bismuth ferrite (BiFeO$_3$), sodium niobate NaNbO$_3$, bismuth titanate Bi$_4$Ti$_3$O$_{12}$, and sodium bismuth titanate Na$_{0.5}$Bi$_{0.5}$TiO$_3$.

For applications in which the medium is a living organism such as a human or an animal, acoustic computing element 200 is fully immersed in a biocompatible encapsulant 218 to isolate its component parts from the patient and prevent irritation and rejection. Encapsulant 218 may be implemented as a bio compatible plastic that includes, but is not limited to polyvinylchloride (PVC), polytetrafluoroethylene (PTFE), polyethylene (PE) and medical grade silicone.

Figure 3:
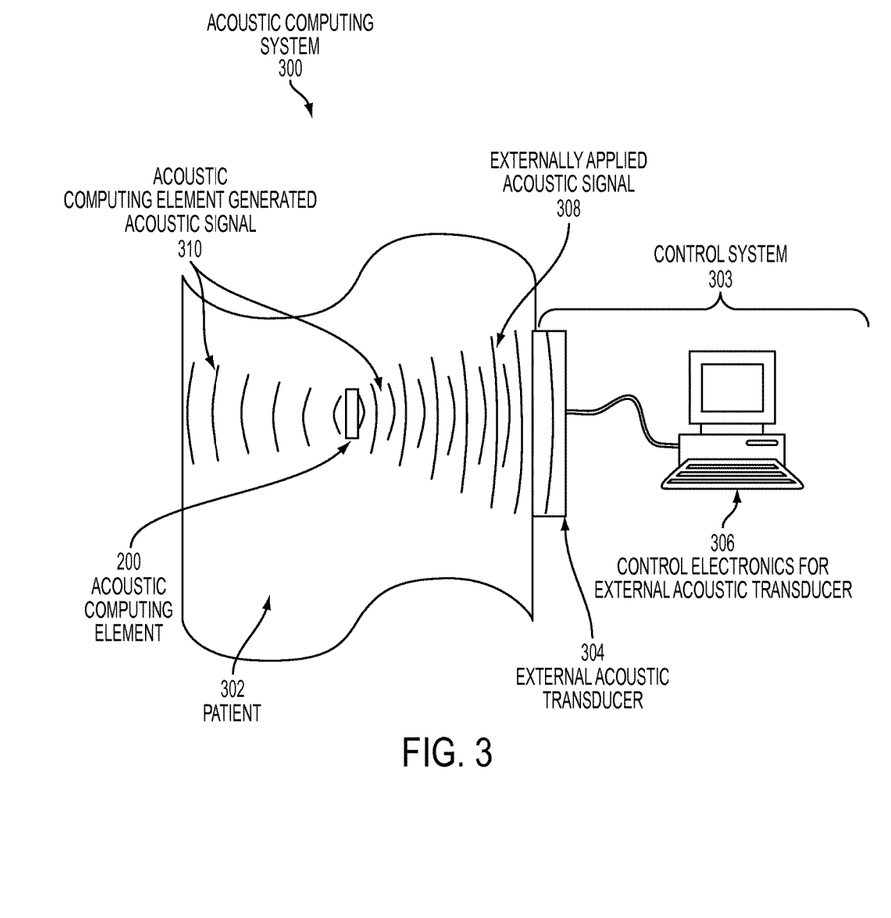
FIG. 3 is a schematic diagram of an implanted acoustic computing system in accordance with one or more embodiments.

FIG. 3 is a schematic diagram of an implant/dermal acoustic computing system 300 in accordance with one or more embodiments. As shown in FIG. 3, implant/dermal acoustic computing system 300 includes implant/dermal acoustic computing element 200 inside a patient 302, a control system 303 formed from an external transducer 304 and control electronics 306, externally applied input acoustic signals 308, and acoustic computing element generated acoustic signals 310, configured and arranged as shown. Implant/dermal acoustic computing element 200 is surgically implanted in patient 302. External acoustic transducer 304 is applied to the exterior of patient 302. An impedance matching gel (not shown) may be applied to acoustically interface external acoustic transducer 304 to patient 302, thereby facilitating the transmission and reception of acoustic vibration from patient 302 and external acoustic transducer 304.

Figure 5:
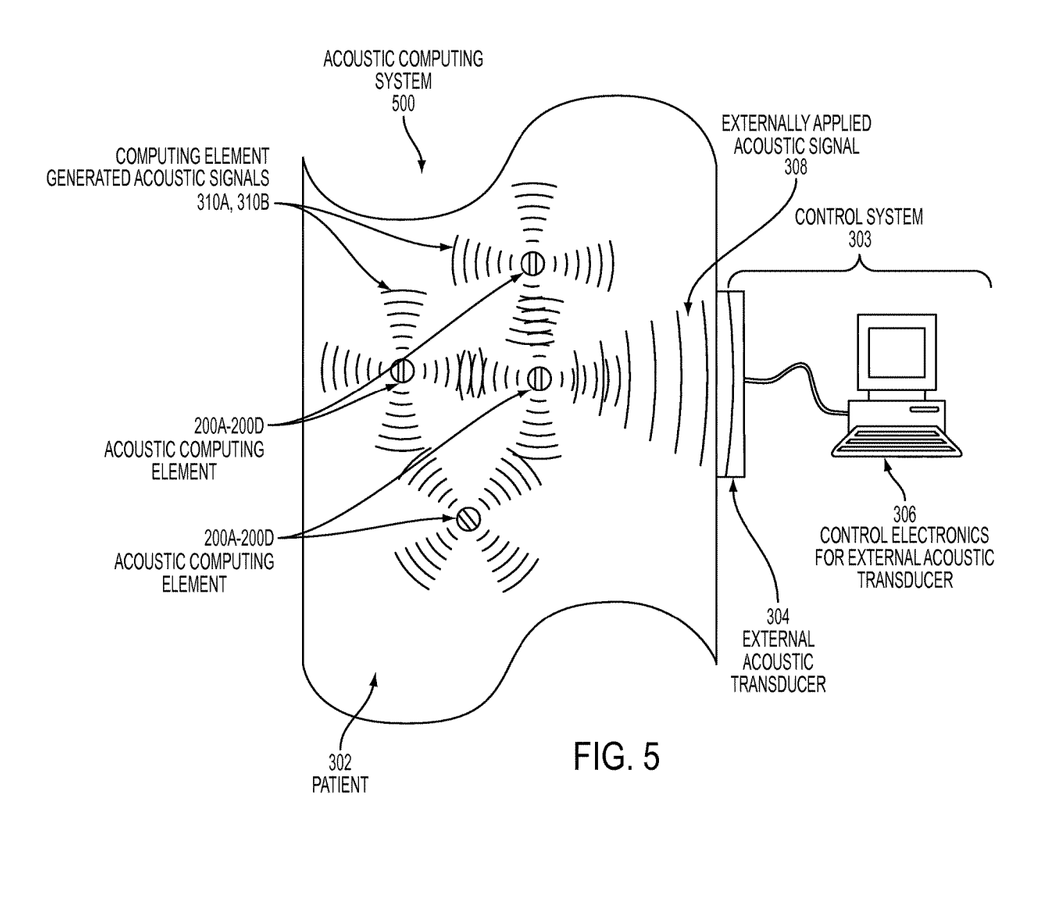
FIG. 5 is a schematic diagram of an acoustic computing network in accordance with one or more embodiments.
Figure 6:
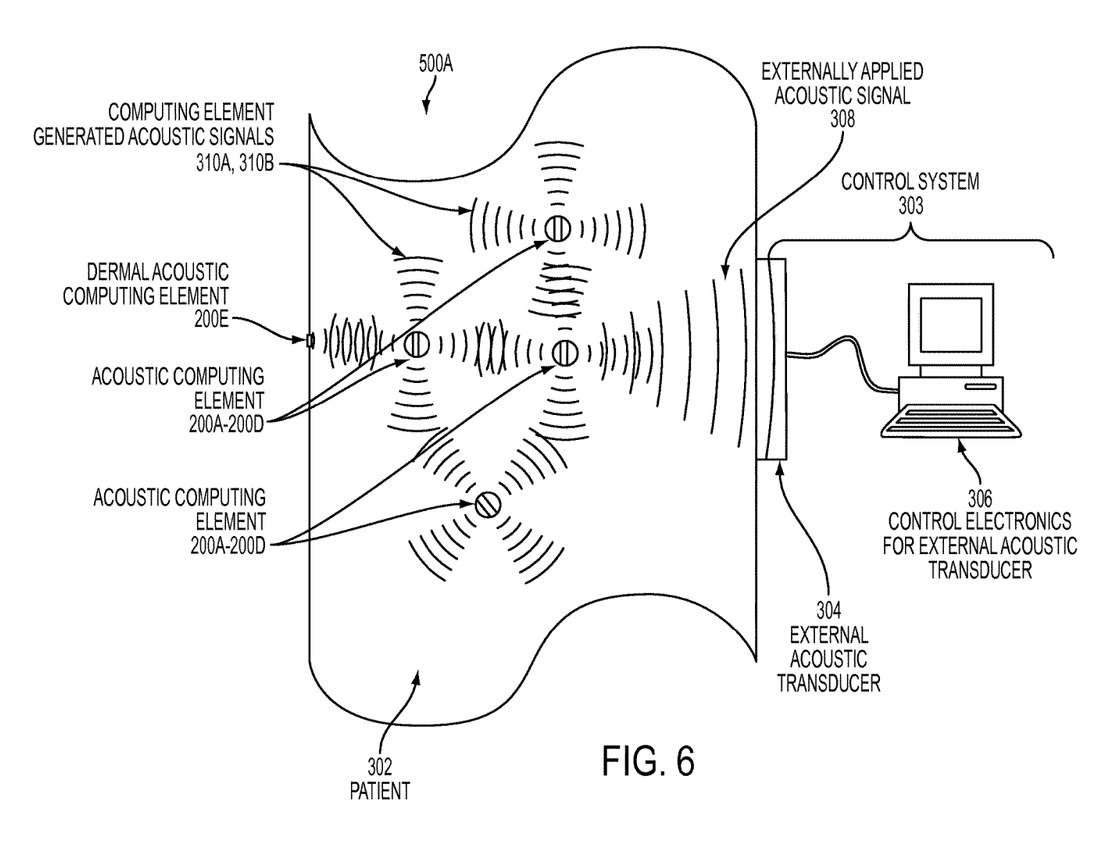
FIG. 6 is a schematic diagram of an implant/dermal acoustic computing network in accordance with one or more embodiments.

External acoustic transducer 304 provides externally applied acoustic signal 308, which provides both energy and instructions/information to implant acoustic computing element 200. In some embodiments, this acoustic emission may be focused, which is shown in FIGS. 3, 5 and 6 by the curvature of the lines that represent externally applied acoustic signals 308 and computing element generated acoustic signals 310, 310A and 310B. Focusing the acoustic emission concentrates energy and enables the detection of very small amplitude signals. This further allows external acoustic transducer 304 to pump a large volume of acoustic energy into implant/dermal acoustic computing element 200 very rapidly, and concentrate the input acoustic energy to a very small volume.

Implant acoustic computing element 200 receives the externally applied acoustic signals 308 and transforms them to electric power to operate implant acoustic computing element 200. In addition, signal processor 206 (shown in FIG. 2) of implant acoustic computing element 200 interprets any information contained in externally applied acoustic signals 308. Signal processor 206 of implant acoustic computing element 200 responds by emitting acoustic computing element generated acoustic signals 310, which propagate through patient 302 and are received by external acoustic transducer 304 and interpreted by control electronics 306. Thereby, acoustic computing system 300 exchanges information between the outside of patient 302 and the inside of the patient 302 where acoustic computing element 200 is located.

Figure 4:
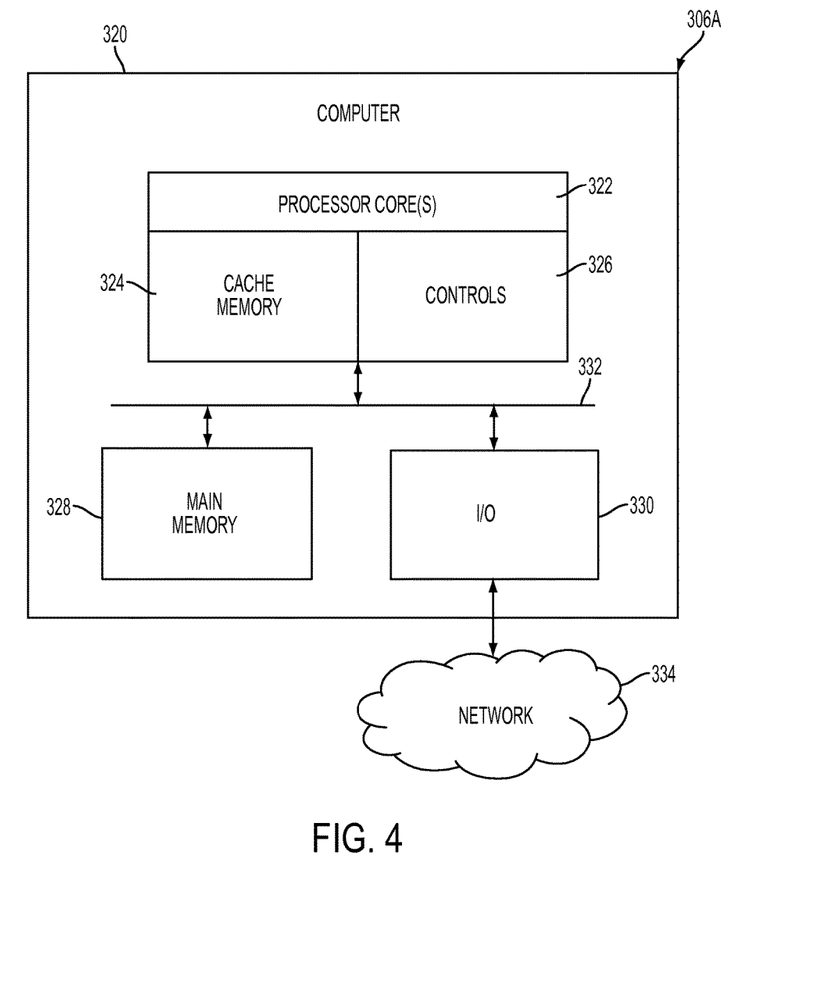
FIG. 4 is a block diagram showing additional details of the control electronics shown in FIG. 3.

FIG. 4 illustrates a more detailed example of how control electronics 306 (shown in FIG. 3) may be implemented as a computer system 306A including an exemplary computing device ("computer") 320 configured to transmit and receive electronic signals from external acoustic transducer acoustic 304 (shown in FIG. 3) in accordance with the present disclosure. In addition to computer 320, exemplary computer system 306A includes network 334, which connects computer 320 to additional systems (not depicted) and may include one or more wide area networks (WANs) and/or local area networks (LANs) such as the Internet, intranet(s), and/or wireless communication network(s). Computer 320 and additional systems are in communication via network 334, e.g., to communicate data between them.

Exemplary computer 320 includes processor cores 322, main memory ("memory") 328, and input/output component(s) 330, which are in communication via bus 332. Processor cores 322 includes cache memory ("cache") 324 and controls 326, which include components configured communicate with and control acoustic computing element(s) 200 (shown in FIG. 1), which will be described in more detail below. Cache 324 may include multiple cache levels (not depicted) that are on or off-chip from processor 322. Memory 324 may include various data stored therein, e.g., instructions, software, routines, etc., which, e.g., may be transferred to/from cache 324 by controls 326 for execution by processor 322. Input/output component(s) 330 may include one or more components that facilitate local and/or remote input/output operations to/from computer 320, such as a display, keyboard, modem, network adapter, etc. (not depicted).

FIG. 5 is a schematic diagram of an acoustic computing network 500 in accordance with one or more embodiments. As shown in FIG. 5, acoustic computing network 500 includes a first implant/dermal acoustic computing element 200A inside patient 302, a second implant/dermal acoustic computing element 200B inside patient 302, a third implant/dermal acoustic computing element 200C inside patient 302, a fourth implant/dermal acoustic computing element 200D inside patient 302, control system 303 formed from external transducer 304 and control electronics 306, externally applied input acoustic signals 308, and acoustic computing element generated acoustic signals 310A, 310B, configured and arranged as shown. Acoustic computing network 500 is similar to acoustic computing system 300 with the addition of the network of acoustic computing elements shown at 200A, 200B, 200C and 200D.

In acoustic computing network 500, individual acoustic computing elements (200A-200D) may communicate directly with each other and with external acoustic transducer 304. Individual acoustic computing elements (200A-200D) may additionally have specialized functions. Examples include acoustic computing elements with a master-slave relationship, sensor monitoring, data collection and medication dispensing. Communication topography between individual acoustic computing elements (200A-200D) may follow a hierarchical arrangement or a mesh.

FIG. 6 is a schematic diagram of an acoustic computing network 500A having implant and dermal acoustic computing elements (200A-200D) in accordance with one or more embodiments. As shown in FIG. 6, acoustic computing network 500A includes a first implant/dermal acoustic computing element 200A inside patient 302, a second implant/dermal acoustic computing element 200B inside patient 302, a third implant/dermal acoustic computing element 200C inside patient 302, a fourth implant/dermal acoustic computing element 200D inside patient 302, a dermal acoustic computing element 200E located on, within or under the dermas of patient 302, a control system formed from external transducer 304 and control electronics 306, externally applied input acoustic signals 308, and acoustic computing element generated acoustic signals 310A, 310B, configured and arranged as shown. Acoustic computing network 500A is similar to acoustic computing network 500 with the addition of dermal acoustic computing element 200E located on, within or under the dermas of patient 302. Dermal acoustic computing element 200E may function in the same manner as the above-described implanted acoustic computing elements 200A-200D. Dermal acoustic computing element 200E is more easily accessed than implanted acoustic computing elements 200A-200D. Although only one dermal acoustic computing element 200E is illustrated, acoustic computing network 500A may include more than one dermal acoustic computing element 200E, and the additional dermal acoustic computing elements may communicate with each other as well as implanted acoustic computing elements (200A-200D) and external acoustic transducer 304. For embodiments wherein dermal acoustic computing element 200E is provided on patient 302, one or more dermal acoustic computing elements may be provided as wearable electronic devices, such as a pendant or wristband in contact with patient 302. In such an embodiment, the wearable electronic devices can power and communicate with each other, and the power source (e.g., external acoustic transducer 304) and the acoustic computing elements may be in contact with the dermis of patient 302.

Although the present disclosure is primarily disclosed in connection with use in human subjects, the teachings of the present disclosure may be used in organisms that include but are not limited to animals, reptiles and invertebrates. Additionally, the implant medium may be an aqueous environment or body of water, including oceans, lakes, streams and ponds. In this case one or more transducers are placed in the body of water and read from a surface area. In some cases the external transducer may be immersed in the body of water. The implant medium may also be a pliable solid body such as a gel. The actual medium may be any virtually any material as long as one or more acoustic computing elements can be substantially immersed therein and the material is partially transparent to acoustic signals while the external transducer is placed in proximity to the surface of the material.

Thus it can be seen from the foregoing detailed description that the present disclosure provides a number of technical benefits. Input and output acoustic transmissions carry both energy and data efficiently with relatively low attenuation. Energy and data acoustic transmissions can also occur between the implant/dermal acoustic element, creating a communications network that operates through a medium. The implant/dermal element, after being powered up is free to perform sensory operations, perform actions such as dispensing, or simply return information.

The disclosed acoustic computing system/network is inherently private because it cannot be read or perturbed without the knowledge, consent and cooperation of the patient. Acoustic vibrations (e.g., in the ultrasonic range) are extremely safe for living organisms. Using acoustics to transmit energy/data allows the delivery of high amplitude acoustic vibrations/signals into the system. The implant/dermal acoustic computing elements can store energy, and their power consumption is typically low. Thus, a significant percentage of the input acoustic energy can be stored, thereby allowing an implant/dermal acoustic computing element to run for a very long time (e.g., a year) without needing an additional charge-up. Thus, the disclosed acoustic-based systems demonstrate significant persistence. To conserve power, the present disclosure may be configured to send and receive acoustic vibration/signals at low amplitudes when power is scarce, and can send and receive acoustic vibration/signals at higher amplitudes when power is abundant. For example, communications between implant/dermal acoustic computing elements would be carried out at lower amplitudes, and communications involving the external acoustic transducer would be carried out at higher amplitudes.

Acoustic transmissions may be focused, which concentrates energy and enables the detection of very small amplitude signals. This further allows the external acoustic transducer to pump a large volume of acoustic energy into the implant/dermal acoustic computing elements very rapidly, and concentrate the input acoustic energy to a very small volume.

In some embodiments, various functions or acts may take place at a given location and/or in connection with the operation of one or more apparatuses or systems. In some embodiments, a portion of a given function or act may be performed at a first device or location, and the remainder of the function or act may be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There may be many variations to the diagram or the steps (or operations) described therein without departing from the spirit of the disclosure. For instance, the actions may be performed in a differing order or actions may be added, deleted or modified. Also, the term "coupled" describes having a signal path between two elements and does not imply a direct connection between the elements with no intervening elements/connections therebetween. All of these variations are considered a part of the disclosure.

It will be understood that those skilled in the art, both now and in the future, may make various improvements and enhancements which fall within the scope of the claims which follow.

What is claimed is:

1. A method of implementing an acoustic computing system for implant or dermal data communication, power supply and energy storage, the method comprising:
   providing a first acoustic computing element; and
   focusing input acoustic vibration to concentrate focused input acoustic vibration toward the first acoustic computing element;
   wherein the first acoustic computing element is configured to:
   operate in a medium;
   receive the focused input acoustic vibration;
   convert a first portion of the focused input acoustic vibration to energy that powers an operation of the first acoustic computing element;
   convert a second portion of the focused input acoustic vibration to stored energy of the first acoustic computing element;
   convert a third portion of the focused input acoustic vibration to a first input data that is processed by the first acoustic computing element; and
   generate a first output acoustic vibration.

2. The method of claim 1 further comprising:
   providing a second acoustic computing element housed separately from the first acoustic computing element;
   wherein the second acoustic computing element is configured to operate in the medium.

3. The method of claim 2, wherein:
   the first output acoustic vibration comprises supplemental acoustic vibration; and
   the second acoustic computing element is further configured to:
   receive the supplemental acoustic vibration;
   convert at least a portion of the supplemental acoustic vibration to the stored energy of the second acoustic computing element.

4. A method of implementing an acoustic computing system for implant or dermal data communication, power supply and energy storage, the method comprising:
   configuring a first acoustic computing element to operate in a medium;
   configuring the first acoustic computing element to receive input acoustic vibration; and
   configuring the first acoustic computing element to:
   convert a first portion of the input acoustic vibration to energy that powers an operation of the first acoustic computing element;
   convert a second portion of the input acoustic vibration to stored energy of the first acoustic computing element; and convert a third portion of the input acoustic vibration to a first input data that is processed by the first acoustic computing element;

wherein a length dimension of the first acoustic computing element and a length dimension of a wavelength of the input acoustic vibration are selected to result in an improvement to coupling efficiency of the input acoustic vibration to the first acoustic computing element.

5. The method of claim 4, wherein the medium comprises a live organism.

6. The method of claim 5 further comprising configuring the first acoustic element to be implanted within the live organism.

7. The method of claim 5 further comprising configuring the first acoustic element to operate either within, under or on a dermis of the live organism.

8. The method of claim 4 further comprising configuring the first acoustic computing element to comprise a first sensor configured to measure a parameter of the medium.

9. The method of claim 8, wherein the parameter of the medium is selected from a group consisting of a concentration, a temperature, a pressure, a force, a magnetic field, an electric field, a biomarker and a chemical potential.

10. The method of claim 4 further comprising configuring the first acoustic computing element to comprise a first actuator configured to interact with the medium.

11. The method of claim 10, wherein the interaction with the medium is selected from a group consisting of a mechanical interaction and an electrical interaction.

12. The method of claim 4 further comprising configuring the first acoustic computing element to generate a first output acoustic vibration based on the first input data.

13. The method of claim 12 further comprising configuring a control system to:
transmit the input acoustic vibration into the medium to the first acoustic computing element; and
receive the first output acoustic vibration.

14. A method of implementing an acoustic computing system for implant or dermal data communication, power supply and energy storage, the method comprising:
providing a first acoustic computing element configured to:
operate in a medium;
receive input acoustic vibration;
convert a first portion of the input acoustic vibration to energy that powers an operation of the first acoustic computing element;
convert a second portion of the input acoustic vibration to stored energy of the first acoustic computing element;
convert a third portion of the input acoustic vibration to a first input data that is processed by the first acoustic computing element; and
generate a first output acoustic vibration that includes supplemental acoustic vibration converted from the stored energy of the first acoustic computing element; and
providing a second acoustic computing element housed separately from the first acoustic computing element;
wherein the second acoustic computing element is configured to:
operate in the medium;
receive the first output acoustic vibration including the supplemental acoustic vibration; and
convert a first portion of the supplemental acoustic vibration to stored energy of the second acoustic computing element.

15. The method of claim 14, wherein the first acoustic computing element is further configured to generate and transmit the supplemental acoustic vibration based on an acoustic vibration communication between the first acoustic computing element and the second acoustic computing element, wherein the acoustic vibration communication represents a request for supplemental acoustic vibration.

16. The method of claim 14, wherein the second acoustic computing element is further configured to:
convert at least a portion of the first output acoustic vibration to second input data that is processed by the second acoustic computing element;
activate, based at least in part on the second input data, an actuator of the second acoustic computing element, wherein the actuator is configured to interact with the medium.

17. The method of claim 14, wherein the second acoustic computing element is further configured to:
convert at least a portion of the first output acoustic vibration to a second input data that is processed by the second acoustic computing element; and
generate and transmit, based at least in part on the second input data, a second output acoustic vibration.

18. The method of claim 17, wherein the second output acoustic vibration is modulated with instructions for a control system.

19. The method of claim 18, wherein the control system is external to the medium.

* * * * *